United States Patent [19]

Henrick

[11] 4,238,614
[45] Dec. 9, 1980

[54] PYRIDYL ESTERS OF ETHER AND THIOETHER SUBSTITUTED CYCLOPROPANECARBOXYLIC ACIDS

[75] Inventor: Clive A. Henrick, Palo Alto, Calif.
[73] Assignee: Zoecon Corporation, Palo Alto, Calif.
[21] Appl. No.: 71,336
[22] Filed: Aug. 30, 1979
[51] Int. Cl.³ ............... C07D 213/64; C07D 213/50
[52] U.S. Cl. .................................. 546/301; 546/302; 546/314; 546/270; 424/263
[58] Field of Search ............ 546/301, 302, 314, 270; 424/263

[56] References Cited

U.S. PATENT DOCUMENTS

| | | |
|---|---|---|
| 3,961,070 | 6/1976 | Davis et al. |
| 3,962,458 | 6/1976 | Schrider ........................... 424/304 |
| 3,979,519 | 7/1976 | Punja .................................. 424/304 |
| 4,163,787 | 8/1979 | Malhotra et al. ................... 546/301 |

OTHER PUBLICATIONS

Harding et al., Chem. Abst. vol. 87, 1977, 87:147002g.
Muirhead-Thomson, Chem. Abstracts, 1977, 87:147018s.
Wood et al., Chem. Abstracts, 1977, 87:134690e.
Matsuo et al., Chem. Abstracts, 1973, vol. 78, 84072w.

*Primary Examiner*—Henry R. Jiles
*Assistant Examiner*—Jane T. Fan

[57] ABSTRACT

Pyridyl esters of ether and thioether substituted cyclopropanecarboxylic acids, synthesis thereof, and intermediates therefor, such esters being useful as pesticides.

20 Claims, No Drawings

PYRIDYL ESTERS OF ETHER AND THIOETHER SUBSTITUTED CYCLOPROPANECARBOXYLIC ACIDS

This invention relates to novel esters of substituted cyclopropane carboxylic acid, synthesis thereof and intermediates therefor, such esters being useful as pesticides.

The novel compounds of the present invention are represented by the following generic formula (A):

$$R^1-W-CH-CH-\underset{\underset{X}{\overset{O}{\overset{\|}{C}}}\underset{X'}{}}{C}-W'-CH-\underset{R^2}{\overset{N}{\bigcirc}}-R-\bigcirc-R'_p \quad (A)$$

wherein,
 W is oxygen or sulfur;
 W' is oxygen or sulfur;
 X is lower alkyl or halogen;
 X' is hydrogen, lower alkyl or halogen;
 R is oxygen, sulfur, methylene or carbonyl;
 R' is fluoro, bromo, chloro, trifluoromethyl, methyl, methoxy or methylthio; p is zero, one or two;
 $R^1$ is s lower alkyl, lower haloalkyl, lower alkenyl, lower haloalkenyl, or the group $$\underset{Z}{\overset{Y_t}{\bigcirc}}$$

in which
 t is zero, one, two, three or four;
 Y is independently selected from hydrogen, lower alkyl, lower haloalkyl, lower alkoxy, lower alkylthio, lower alkylcarbonyl, lower alkoxycarbonyl, lower acyloxy, halogen, cyano, nitro and lower haloalkylthio;
 Z is independently selected from the values of Y, cycloalkyl and lower haloalkoxy; or together with Y forms a methylenedioxy group; and
 $R^2$ is hydrogen, cyano, ethynyl, methyl or ethyl.

The compounds of the present invention represented by generic formula (A) are useful agents for the control of pests such as insects and acarids. Without any intention of being bound by theory and although the mode of action of the compounds of formula (A) as applied to the control of insects and acarids is not completely understood, the compounds of formula (A) appear to be effective for the control of insects and acarids by reason of mechanisms of the nature of the insect control agents know as pyrethrins and synthetic pyrethroids.

In the description hereinafter and the appended claims, each of R—$R^2$, W, W', X, X', Y, Z, P, and t is as defined hereinabove, unless otherwise specified.

The compounds of formula (A) can be prepared by the reaction of an acid of formula I or the acid halide thereof with an alcohol of formula IA. For example, the acid I is reacted with thionyl chloride in the presence of a solvent such as hexamethylphosphoric triamide (HMPT), dimethylformamide (DMF), tetrahydrofuran (THF) and the like, and then with the alcohol in the presence of a catalyst such as 4-dimethylaminopyridine.

Alternatively, an acid of formula I is reacted with the halide, e.g., bromide, or mesylate corresponding to the alcohol IA in the presence of a base such as potassium carbonate and the like in an organic solvent to prepare the esters of formula (A).

$$R^1-W-CH-CH-\underset{\underset{X}{\overset{\|}{C}}\underset{X'}{}}{\overset{O}{C}}-OH \qquad HO-CH-\underset{R^2}{\overset{N}{\bigcirc}}-R-\bigcirc-R_p'$$

(I)  (IA)

The acids of formula I can be made as described in my copending application Ser. No. 942,509, filed Sept. 15, 1978 now U.S. Pat. No. 4,198,527. Alcohols of formula IA wherein $R^2$ is hydrogen, cyano or ethynyl and R is oxygen or sulfur can be prepared according to the procedures of Malhotra and Ricks, U.S. Pat. No. 4,163,787. The thiols corresponding to the alcohols of formula A can be prepared by conversion of the alcohol to the bromide using, for example, phosphorus tribromide. The bromide is then converted to a lower alhyl thio-ester using thio-acetic acid or the like which on treatment with lithium aluminum hydride gives the thiol. The thiol is reacted with the acid chloride of an acid of formula (I) to prepare the S-thioesters of the present invention (A; W' is sulfur.)

The following terms, wherever used in the description herein and the appended claims, have the meaning defined below, unless otherwise specified hereinafter.

The term "lower alkyl" refers to an alkyl group, straight or branched, having a chain length of one to six carbon atoms. The term "lower haloalkyl" refers to an alkyl group substituted with one to three halogen atoms such as chloromethyl, fluoromethyl, trifluoromethyl, 2,2,2-trifluoroethyl, 6-chlorohexyl, 2-fluoroethyl, and the like. The term "lower alkoxy" refers to an alkoxy group, straight or branched, having a chain length of one to six carbon atoms. The term "lower alkylthio" refers to an alkylthio group, straight or branched, having a chain length of one to six carbon atoms.

The term "lower alkenyl" refers to an ethylenically unsaturated hydrocarbon group, straight or branched, having a chain length of two to six carbon atoms and one or two ethylenic bonds such as vinyl, allyl, 3-butenyl, 2-hexenyl, i-propenyl, 2,4-hexadienyl, and the like. The term "lower haloalkenyl" refers to a lower alkenyl group substituted with one to three halogen atoms.

The term "cycloalkyl" refers to a cycloalkyl group of three to six cyclic carbon atoms.

The term "halogen" refers to bromo, chloro, fluoro or iodo.

The term "lower haloalkoxy" refers to a lower alkoxy group substituted with one to three halogen atoms.

The term "lower acyloxy" refers to a lower organic acyloxy group of one to six carbon atoms, such as acetoxy.

The compounds of the present invention of formula (A) have one or more asymmetric carbon atoms. The present invention includes each of the optical isomers and racemic mixtures thereof. In the examples hereinafter, unless otherwise specified, the compound prepared is a racemic mixture.

The compounds of the present invention of formula(A) are useful pest control agents, particularly for the control of insects and acarids. In the use of the compounds of formula (A) for combatting insects and acarids for the protection of agricultural crops, for example soybeans, cotton, alfalfa, etc., a compound of formula (A), or mixtures thereof, together with a carrier is applied to the locus in a pesticidally effective amount. The carrier can be liquid or solid and include adjuvants such as wetting agents, dispersing agents and other surface active ingredients. The compounds of formula (A) can be used in formulations such as wettable powders, solutions, dusts, granules, emulsifiable concentrates, and the like. Suitable solid carriers include natural and synthetic silicates and clays, carbon or charcoal granules, natural and synthetic resins, waxes, and the like. Suitable liquid carriers include water, aromatic hydrocarbons, alcohols, vegetable and mineral oils, ketones, and the like. The amount of a compound of formula (A) in the formulation can vary widely, generally within the range of about 0.01 percent to about 90.0 percent, by weight, more usually 0.01 to 25.0 percent.

The compounds of the present invention can be used in combination with other pesticides such as the carbamates, phosphates and insect growth regulators, e.g., propoxur, carbaryl, naled, dichlorvos, phosmet, chlorpyrifos, acephate, diazinon, methoprene, kinoprene, hydroprene, cyhexatin, resmethrin, permethrin and fenvalerate.

The following examples are provided to illustrate the practice of the present invention. Temperature is given in degrees Centigrade. RT means room temperature.

EXAMPLE 1

To a solution of 3-(4-chlorophenoxy)-2,2-dimethylcyclopropanecarboxylic acid (0.244 g, 1.01 mmol) in 10 ml. of benzene is added 0.19 g of oxalylchloride (1.5 mmol) followed by 3-4 drops of DMF. The reaction mixture is stirred for about 4 hours, stripped of solvent and excess oxalyl chloride and about 10 ml of ether is added. A solution of (6-phenoxy-2-pyridyl) methanol (0.20 g, 0.99 mmol) and triethylamine (1.08 mmol) in 5 ml. of ether is added and the reaction mixture stirred for about 12 hours. The mixture is then diluted with ether and aqueous $NaHCO_3$. The organic phase is washed with $NaHCO_3$ solution, water and saturated aqueous NaCl, dried over $Ca SO_4$ and solvent evaporated. The crude product is chromatographed on a circular chromatograph eluting with 10 percent ether/hexane to yield (6-phenoxy-2-pyridyl) methyl 3-(4-chlorophenoxy)-2,2-dimethylcycolopropanecarboxylate, MS m/e 423 (M+).

EXAMPLE 2

To a mixture of cyano (6-phenoxy-2-pyridyl) methanol (0.211 g, 0.993 mmol), 3-(4-chlorophenoxy)-2,2-dimethylcyclopropanecarboxylic acid (0.253 g, 1.05 mmol), and dimethylaminopyridine (0.012 g, 0.10 mmol), with stirring, is added N,N'-dicyclohexylcarbodiimide (0.195 g, 0.945 mmol). The reaction mixture is stirred for about 90 minutes and then filtered. The filtrate is diluted with ether, washed with saturated aqueous $NaHCO_3$, water and brine, dried over $Ca SO_4$ and solvent evaporated. The crude product is chromatographed on plates using 20 percent ether/hexane to yield cyano (6-phenoxy-2-pyridyl) methyl 3-(4-chlorophenoxy)-2,2-dimethylcyclopropanecarboxylate, MS m/e 448 (M+).

EXAMPLE 3

To 30 ml of methylene chloride is added cyano (6-phenoxy-2-pyridyl) methanol (0.44 g, 2.15 mmol), dimethylaminopyridine (0.32 g, 2.58 mmol), 3-(n-butoxy)-2,2-dimethylcyclopropanecarboxylic acid (0.4 g, 2.15 mmol) and N,N'-dicyclohexylcarbodiimide (0.44 g, 2.15 mmol). The reaction mixture is stirred for about 18 hours and then worked up as in Example 2. The crude product is purified using thin layer chromatography (20% ethyl acetate/hexane) yielding cyano (6-phenoxy-2-pyridyl) methyl 3-(n-butoxy)-2,2-dimethylcyclopropanecarboxylate, MS m/e 394 (M+).

EXAMPLE 4

To a mixture of benzene (10 ml) and 3-(n-butoxy)-2,2-dimethylcyclopropanecarboxylic acid (1.1 mmol) is added oxalyl chloride (1.8 mmol) and 2-3 drops of DMF. After evolution of gas has stopped (about 5-10 minutes), the mixture is warmed to about 40. Then the mixture is stripped of solvent and excess oxalyl chloride. To the reaction product is added THF and then (6-phenoxy-2-pyridyl) methanethiol (0.92 mmol) and dimethylaminopyridine (1.84 mmol), with stirring. The reaction mixture is stirred for about 18 hours. The reaction is worked up by addition of ether followed by working with water and brine, drying over sodium sulfate and evaporating of solvent. The crude product is chromatographed on plates using 20 percent ethylacetate/hexane to yield S-(6-phenoxy-2-pyridyl) methylthioester of 3-(n-butoxy)-2,2-dimethylcyclopropanecarboxylic acid.

(6-Phenoxy-2-pyridyl) methanethiol is prepared from (6-phenoxy-2-pyridyl) methanol as follows: To (6-phenoxy-2-pyridyl) methanol (0.3 g, 1.49 mmol) in 20 ml of ether is added phosphorus tribromide (0.60 g, 2.23 mmol) at 5. The mixture is stirred for 20 minutes at 5 and then allowed to warm to RT over about 1 hour. The mixture is heated reflux and additional $PBr_3$ (0.2 ml) added. The reaction mixture is refluxed for 2 hours. After no starting alcohol is detected by thin layer chromatography, the reaction is cooled to RT, filtered and the solid washed with dry ether. The solid, HBr salt of (6-phenoxy-2-pyridyl) methyl bromide is pumped dry.

To cooled (5°) mixture of 20 ml of ether and washed NaH (1.91 mmol) is added thio-acetic acid (1.91 mmol). The mixture is stirred for 15 minutes at RT and after cooling to about 5°, the HBr salt of (6-phenoxy-2-pyridyl) methyl bromide (0.869 mmol) is added. This reaction mixture is allowed to warm to RT and then stirred for about 48 hours. The reaction is taken up in ether, washed with 5 percent NaOH, water, and brine, dried over sodium sulfate and solvent evaporated to yield S-(6-phenoxy-2-pyridyl) methyl thioester of acetic acid. The thus-obtained thioacetate (0.21 g, 0.863 mmol) is added to 15 ml of ether containing lithium aluminum hydride (1.29 mmol), at 5°. The reaction mixture is stirred at RT for 5 hours and then quenched by adding water and dilute NaOH. The reaction is worked up by filtering through celite and stripping the filtrate of solvent to yield the thiol product—(6-phenoxy-2-pyridyl) methane thiol.

EXAMPLE 5

To a mixture of 3-(n-pentyloxy)-2,2-dimethylcyclopropanecarboxylic acid (2.63 mmol), cold methylene chloride (5 ml) and dimethylaminopyridine (0.21 mmol) is added α-methyl (6-phenoxy-2-pyridyl) methanol (2.79 mmol) in 2 ml of methylene chloride at 0°. After brief stirring, N,N'-dicyclohexylcarbodiimide (2.6 mmol) is added. The reaction mixture is stirred for about 4 hours at RT and then filtered. The filtrate is stripped of methylene chloride and the residue taken up in ether and filtered. The filtrate is washed with saturated NaHCO$_3$, water and brine, dried, and solvent evaporated under vacuum to yield α-methyl (6-phenoxy-2-pyridyl) methyl 3-(n-pentyloxy)-2,2-dimethylcyclopropanecarboxylate.

The alcohol, 2-methyl(6-phenoxy-2-pyridyl) methanol is prepared by oxidation of (6-phenoxy-2-pyridyl) methanol using chromium trioxide-pyridine to the aldehyde, 6-phenoxypyridyl-2-carboxaldehyde, which by grignard reaction using methyl magnesium bromide in THF provides the desired alcohol.

EXAMPLE 6

2-methyl-6-pyridinecarboxylic acid is converted to the acid chloride using oxalyl chloride in benzene which on treatment with aluminum chloride in benzene provides (6-benzoyl-2-methyl) pyridine. To a mixture of (6-benzoyl-2-methyl) pyridine (3.9 g) and 20 ml of chloroform is added m-chloroperbenzoic acid (4.2 g) in 50 ml. of chloroform over about 1 hour. The reaction mixture was stirred overnight and then diluted with chloroform to about 130 ml. The reaction is then washed with saturated NaHSO$_3$, water, 20 percent NaHCO$_3$ and water, dried, and solvent stripped to isolate reaction product, white solid. The reaction product is added slowly to acetic anhydride (6.6 ml) heated to 115°. After addition complete (about 1.5 hours) and reaction cooled, the reaction is poured onto about 100 g of ice which is then extracted with ether. The ether extracts are combined, washed with saturated NaHCO$_3$ and water to neutral, dried and solvent removed to yield the acetate of (6-benzoyl-2-pyridyl) methanol. The acetate is hydrolyzed using KOH in methanol to obtain the alcohol.

Using the procedure of Example 1, 3-(n-pentyloxy)-2,2-dimethylcyclopropanecarboxylic acid is reacted with (6-benzoyl-2-pyridyl) methanol to yield (6-benzoyl-2-pyridyl) methyl 3-(n-pentyloxy)-2,2-dimethylcyclopropanecarboxylate.

EXAMPLE 7

Following the procedure of Example 2, each of 3-(i-butoxy)-2,2-dimethylcyclopropanecarboxylic acid, 3-(n-propoxy)-2,2-dimethylcyclopropanecarboxylic acid, 3-(n-but-2-enoxy)-2,2-dimethylcyclopropanecarboxylic acid, 3-(3-fluoropropenoxy)-2,2-dimethylcyclopropanecarboxylic acid, 3-(2,2,2-triflouroethoxy)-2,2-dimethylcyclopropanecarboxylic acid, is reacted with cyano-(6-phenoxy-2-pyridyl) methanol to yield cyano (6-phenoxy-2-pyridyl) methyl 3-(i-butoxy)-2,2-dimethylcyclopropanecarboxylate, cyano (6-phenoxy-2-pyridyl) methyl 3-(n-but-2-enoxy)-2,2-dimethylcyclopropanecarboxylate, cyano (6-phenoxy-2-pyridyl) methyl 3-(3-flouropropenoxy)-2,2-dimethylcyclopropanecarboxylate and cyano (6-phenoxy-2-pyridyl) methyl 3-(2,2,2-triflouroethoxy)-2,2-dimethylcyclopropanecarboxylate.

EXAMPLE 8

Using the procedure of Example 5, each of 3-(4-fluorophenoxy)-2,2-dimethylcyclopropanecarboxylic acid, 3-phenylthio-2,2-dimethylcyclopropanecarboxylate, 3-(n-propylthio)-2,2-dimethylcyclopropanecarboxylic acid, 3-phenoxy-2,2-dichlorocyclopropanecarboxylic acid and 3-(2-fluoro-4-trifluoromethylphenoxy)-2,2-dimethylcyclopropanecarboxylic acid is reacted with α-ethynyl (6-phenoxy-2-pyridyl) methanol to yield α-ethynyl (6-phenoxy-2-pyridyl) methyl 3-(4-fluorophenoxy)-2,2-dimethylcyclopropanecarboxylate, α-ethynyl (6-phenoxy-2-pyridyl) methyl 3-phenylthio-2,2-dimethylcyclopropanecarboxylate, α-ethynyl (6-phenoxy-2-pyridyl) methyl 3-(n-propylthio)-2,2-dimethylcyclopropanecarboxylate, α-ethynyl (6-phenoxy-2-pyridyl) methyl 3-phenoxy-2,2-dichlorocyclopropanecarboxylate, and α-ethynyl (6-phenoxy-2-pyridyl) methyl 3-(2-fluoro-4-trifluoromethylphenoxy)-2,2-dimethylcyclopropanecarboxylate.

EXAMPLE 9

To the acid chloride of 3-(n-pentyloxy)-2,2-dimethycyclopropanecarboxylic acid (3.9 mmol) in 50 ml. of benzene is added (6-phenylthio-2-pyridyl) methanol (3.9 mmol) and 4,4-dimethylaminopyridine (3.9 mmol). The reaction mixture is stirred at 25° for about 14 hours. The mixture is then poured into water and extracted with ether. The organic phase is washed with diluted HCl, saturated NaHCO$_3$, water and brine, dried over sodium sulfate and solvent removed to yield (6-phenylthio-2-pyridyl) methyl 3-(n-pentyloxy)-2,2-dimethylcyclopropanecarboxylate.

EXAMPLE 10

Following the procedure of Example 3, each of α-cyano-[(4-fluoro-6-phenoxy)-2-pyridyl] methanol, α-methyl-[(4-fluoro-6-phenoxy)-2-pyridyl] methanol, α-cyano-[(3-methoxy-6-phenoxy)-2-pyridyl] methanol, α-cyano-[(3,4-dimethyl-6-phenoxy)-2-pyridyl] methanol and α-cyano (6-benzoyl-2-pyridyl) methanol is reacted with 3-(n-pentyloxy)-2,2-dimethylcyclopropanecarboxylic acid to yield α-cyano-[(4-fluoro-6-phenoxy)-2-pyridyl] methyl 3-(n-pentyloxy)-2,2-dimethylcyclopropanecarboxylate, α-methyl-[(4-fluoro-6-phenoxy)-2-pyridyl] methyl 3-(n-pentyloxy)-2,2-dimethylcyclopropanecarboxylate, α-cyano-[(3-methoxy-6-phenoxy)-2-pyridyl] methyl 3-(n-pentyloxy)-2,2-dimethylcyclopropanecarboxylate, α-cyano-[(3,4-dimethyl-6-phenoxy)-2-pyridyl] methyl 3-(n-pentyloxy)-2,2-dimethycyclopropanecarboxylate and α-cyano-(6-benzoyl-2-pyridyl) methyl 3-(n-pentyloxy)-2,2-dimethylcyclopropanecarboxylate.

EXAMPLE 11

Following the procedure of Example 4, the thiol, (6-phenoxy-2-pyridyl) methanethiol, is reacted with the acid chloride of 3-(4-chlorophenoxy)-2,2-dimethylcyclopropanecarboxylic acid, 3-(4-methylphenoxy)-2,2-dimethylcyclopropanecarboxylic acid, and 3-(n-but-2-enoxy)-2,2-dimethylcyclopropanecarboxylic acid to yield the corresponding S-thioester.

Two groups of 10 each of 0–24 hour III instar *Heliothis virescens* larvae were treated with 1 ul of the compound, cyano (6-phenoxy-2-pyridyl) methyl 3-(4- chlorophenoxy)-2,2-dimethyl-cyclopropanecarboxylate in acetone at five different concentrations by application to the dorsum of the thorax. Two groups of 10 each are treated identically with 1 ul acetone only as controls. Larvae are held individually in 30 ml plastic cups provided with artificial medium for 72 hours at 25 and 16 hour photoperiod. After 72 hour the number of dead is calculated as a percentage of the total number originally treated and then corrected for any mortality in the control groups using Abbott's formula. The $LC_{50}$ of the compound was less than 0.05%.

What is claimed is:

1. A compound of the formula (A):

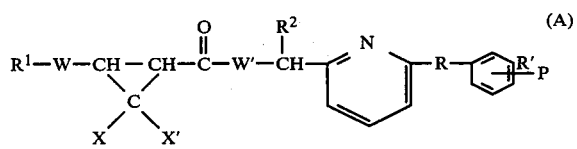

wherein,

W is oxygen or sulfur;

W' is oxygen or sulfur;

X is lower alkyl or halogen;

X' is hydrogen, lower alkyl or halogen;

R is oxygen, sulfur, methylene or carbonyl;

R' is fluoro, bromo, chloro, trifluoromethyl, methyl, methoxy, or methylthio; p is zero, one or two;

$R^1$ is lower alkyl, lower haloalkyl, lower alkenyl, lower haloalkenyl, or the group

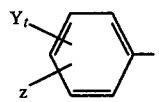

in which t is zero, one, two, three or four;

Y is independently selected from hydrogen, lower alkyl, lower haloalkyl, lower alkoxy, lower alkylthio, lower alkylcarbonyl, lower alkoxycarbonyl, lower alkanogoxy, halogen, cyano, nitro and lower haloalkylthio;

Z is independently selected from the values of Y, cycloalkyl of three to six carbon atoms and lower haloalkoxy; and $R^2$ is hydrogen, cyano, ethynyl, methyl or ethyl.

2. A compound according to claim 1 wherein $R^1$ is the group

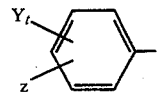

and t is zero or one;

3. A compound according to claim 2 wherein Z is hydrogen, chloro, fluoro, bromo, trifluoromethyl, lower alkyl of 1 to 4 carbon atoms, lower alkoxy of 1 or 2 carbon atoms or lower alkylthio of 1 or 2 carbon atoms and each of X and X' is methyl.

4. A compound according to claim 3 wherein Z is in the para position.

5. A compound according to claim 4 wherein p is zero or one, R' is fluoro, and $R^2$ is hydrogen, methyl or cyano.

6. A compound according to claim 5 wherein each of W and W' is oxygen.

7. A compound according to claim 6 wherein R is oxygen.

8. A compound according to claim 7 wherein R is carbonyl.

9. A compound according to claim 5 wherein W is oxygen and W' is sulfur.

10. A compound according to claim 9 wherein R is oxygen or carbonyl and $R^2$ is hydrogen.

11. A compound according to claim 1 wherein $R^1$ is lower alkyl and each of X and X' is methyl.

12. A compound according to claim 11 wherein R' is fluoro, p is zero or one, W is oxygen, R is oxygen or carbonyl, and $R^2$ is hydrogen, methyl or cyano.

13. A compound according to claim 12 wherein each of W' and R is oxygen and $R^1$ is a primary or secondary lower alkyl group.

14. A compound according to claim 12 wherein W' is oxygen, R is carbonyl and $R^1$ is a primary or secondary lower alkyl group.

15. A compound according to claim 14 wherein $R^2$ is hydrogen.

16. A compound according to claim 11 wherein W' is sulfur, R' is fluoro, p is zero or one, $R^2$ is hydrogen, R is oxygen or carbonyl and $R^1$ is a primary or secondary lower alkyl group.

17. The compound, cyano(6-phenoxy-2-pyridyl)-methyl 3-(4-chlorophenoxy)-2,2-dimethylcyclopropanecarboxylate, according to claim 2.

18. The compound, cyano (6-phenoxy-2-pyridyl)-methyl 3-(n-butoxy)-2,2-dimethylcyclopropanecarboxylate, according to claim 12.

19. The compound, S-(6-phenoxy-2-pyridyl)methyl-thioester of 3-(n-butoxy)-2,2-dimethylcyclopropanecarboxylic acid, according to claim 12.

20. The compound, α-methyl(6-phenoxy-2-pyridyl)-methyl 3-(n-pentyloxy)-2,2-dimethylcyclopropanecarboxylate, according to claim 12.

* * * * *